(12) United States Patent
Redd et al.

(10) Patent No.: US 7,730,847 B1
(45) Date of Patent: Jun. 8, 2010

(54) PERSONAL, WEARABLE, DISPOSABLE BREATHING-GAS FLOW INDICATOR

(76) Inventors: Iris H. Redd, 10212 Pollard Creek Rd., Mechanicsville, VA (US) 23116; John L. Redd, 10212 Pollard Ck, Mechanicsville, VA (US) 23116

( * ) Notice: Subject to any disclaimer, the term of this patent is extended or adjusted under 35 U.S.C. 154(b) by 643 days.

(21) Appl. No.: 11/599,069

(22) Filed: Nov. 14, 2006

Related U.S. Application Data

(63) Continuation-in-part of application No. 10/243,318, filed on Sep. 12, 2002, now Pat. No. 7,159,533.

(51) Int. Cl.
*G01F 15/04* (2006.01)
(52) U.S. Cl. .................. 116/274; 116/264; 116/112; 128/205.23
(58) Field of Classification Search .............. 116/274, 116/276, 271, 273, 264, 266, 112; 96/416, 96/417, 422; 55/DIG. 34; 128/205.23, 205.15, 128/205.18; 222/40
See application file for complete search history.

(56) References Cited

U.S. PATENT DOCUMENTS

| | | | |
|---|---|---|---|
| 799,603 | A | 9/1905 | King |
| 1,783,379 | A | 1/1930 | Jacob |
| 1,783,644 | A | 12/1930 | Geyer |
| 4,098,271 | A | 7/1978 | Maddock |
| 4,188,946 | A | 2/1980 | Watson |
| 4,745,877 | A | 5/1988 | Chang |
| 4,790,832 | A | 12/1988 | Lopez |
| 5,092,809 | A | 3/1992 | Kessler |
| 5,293,864 | A | 3/1994 | McFadden |
| 5,320,092 | A | 6/1994 | Ryder |
| D348,753 | S | 7/1994 | Stojanovski |
| 5,374,239 | A | 12/1994 | Mischenko |
| 5,937,852 | A | 8/1999 | Butler |
| 5,944,054 | A | 8/1999 | Saieva |
| 5,979,442 | A | 11/1999 | Orr |
| 6,073,628 | A | 6/2000 | Butler |
| 6,386,196 | B1 | 5/2002 | Culton |
| 6,578,571 | B1 | 6/2003 | Watt |
| 2009/0145349 | A1* | 6/2009 | Hebert ....................... 116/264 |

* cited by examiner

*Primary Examiner*—R. A. Smith
*Assistant Examiner*—Tania C Courson

(57) ABSTRACT

A personal gas flow indicator is disclosed in which a flow indicator is interposed between the proximal end of a gas delivery cannula that conducts breathing-gas from a breathing-gas source to an airway interface device (AID) for introducing the breathing-gas into the airway of an patient. By having the gas flow indicator positioned at the proximal end of the gas delivery cannula, the patient or some other person in visual contact with the patient can easily determine whether or not breathing-gas is flowing through the gas delivery cannula. The flow indicator is sufficiently lightweight that it can be worn by the patient. It is both disposable and portable and can be easily retrofit into existing-gas delivery systems. The flow indicator can be incorporated into an AID, into a gas delivery cannula, or it can be easily retrofit into one-piece gas delivery cannulas.

19 Claims, 3 Drawing Sheets

PERSONAL, WEARABLE, DISPOSABLE BREATHING-GAS FLOW INDICATOR

CROSS-REFERENCE TO RELATED APPLICATIONS

This is a continuation-in-part of application Ser. No. 10/243,318, filed on Sep. 12, 2002, now U.S. Pat. No. 7,159,533, granted on Jan. 9, 2007.

BACKGROUND OF THE INVENTION

1. Field of the Invention

The present invention relates generally to medical devices for monitoring the flow of breathing-gases through a gas delivery cannula, and more specifically the invention relates to a personal, disposable, and wearable flow indicator for monitoring the flow of a breathing-gas through a gas delivery cannula.

2. Definitions

The definitions set forth here are provided in order to clarify certain terms used in this disclosure. Examples, where provided, are not meant to limit the scope of the invention, but are provided to illustrate the relevant terms.

Breathing-gas—gaseous oxygen, either alone or admixed with other gases and/or pharmacological agents, that is or is intended to be delivered to the airway of a patient. Air, and more specifically compressed air, is considered a breathing-gas within the scope of the present disclosure and claims.

Patient—An individual who is in need of and/or who consumes a breathing-gas. The term "patient" is used herein not to limit the scope or context of the invention, but rather to emphasize that the most common use of the present invention is within the medical setting.

Personal—"Personal" when used herein refers to those collective characteristics of a flow indicator that allow the flow indicator to be used by a single patient and then disposed of. Such characteristics, as described in detail below, include the ability to easily swap the flow indicator in and out of the breathing-gas delivery system, and the ability to mass produce sufficiently large numbers of the flow indicators that they can be used and disposed of economically.

Breathing-gas source—A breathing-gas source is considered herein to be any device feeding breathing-gas under positive pressure into a gas delivery cannula, as "gas delivery cannula" is defined below. Common examples of breathing-gas sources include a tank containing a breathing-gas under pressure, and a pump that pumps a breathing-gas into a gas delivery cannula. "Breathing-gas source" as used herein includes hardware components "upstream" of the gas delivery cannula, for instance, regulators, meters, metal conduits, and "Christmas tree" connectors. For the purposes of the present disclosure, a gas outlet built into a wall or bulkhead is considered a component of a breathing-gas source.

Proximal and distal—The terms "proximal" and "distal" are used herein with reference to the patient. "Proximal" means towards or near the patient. "Distal" means away from the patient; i.e. towards, at, or near the gas source.

Airway Interface Device (AID)—A device for introducing a breathing-gas into a patient's airway. By way of example, commonly employed AID's include face masks, mouthpieces, nasal cannulas, and endotracheal tubes. An AID may be reversibly separable from the gas delivery cannula or it may be integrated into the gas delivery cannula.

Gas delivery cannula—tubing used to transmit a breathing-gas from a gas source to an AID. Flexible, transparent tubing having an internal diameter of approximately 2.0-4.0 mm is generally used as gas delivery cannulas. However, the term "gas delivery cannula" is used broadly in the present disclosure and claims to include any tubing used to transmit breathing-gas from a gas source to an AID.

Nasal cannula—a specific type of AID that delivers breathing-gas to a person's nasal passages. By way of example, the standard nasal cannula now commonly used consists of tubing that connects at its distal end to the proximal end of the gas delivery cannula and bifurcates to form a loop. The loop incorporates a nose-piece with two outlet ports. The outlet ports are placed adjacent to the patient's nares so that breathing-gas flows out of the outlet ports and directly into the nasal airway of the patient. The nasal cannula is held in place by the loop being placed over the patient's ears, by means of an elastic strap, or by other means not pertinent to the present invention.

Accommodate frictional faying—refers to a characteristic of two elements such that they are designed and manufactured with sufficiently complimentary dimensions and geometry to permit them to be frictionally joined in a secure, air-tight manner.

3. Prior Art

A very common medical situation is one in which it is necessary to deliver a breathing-gas to a patient's airway. A large variety of breathing-gas delivery systems have been designed for this purpose. Although the prior art of such breathing-gas delivery systems is too extensive to inventory here, U.S. Pat. No. 4,188,946 to Watson and Rayburn discloses a representative example.

Such breathing-gas delivery systems comprise a minimum of three elements: 1) a source of the breathing-gas; 2) a gas delivery cannula for transmitting the breathing-gas from the source to the patient, and 3) an AID for introducing the breathing-gas into the patient's airway. Many breathing-gas delivery systems incorporate additional elements incorporated into the breathing-gas source or interposed between the breathing-gas source and the gas delivery cannula. Such elements include metal conduits, "Christmas tree" connectors, wall outlets, flow meters, valves, flow regulators, and the like.

In breathing-gas delivery systems the distal end of the gas delivery cannula is connected to the breathing-gas source. The proximal end of the gas delivery cannula is continuous with or connected to the AID, which introduces the breathing-gas to the patient's airway. As long as breathing-gas is flowing through the system, the patient inhales the delivered breathing-gas as it exits the AID. If the flow of the breathing-gas through the system is cut off, the patient inhales either nothing or only ambient air, which may not have a sufficiently high oxygen content to sustain the patient. Consequently, it is important to be able to ascertain whether or not breathing-gas is flowing all the way through the gas delivery cannula to the patient's airway.

Flow-indicators are commonly used to determine whether breathing-gas is flowing in a breathing-gas delivery system. A common type of flow indicator is a rotary sight flow indicator, which comprises a rotatable member positioned in a chamber that is in communication with the gas source. The rotatable member in the chamber is visible through a window in the flow indicator housing. Gas moving through the chamber causes the rotatable member to rotate, and this provides a visible indication that the gas is moving. A representative general-use rotary sight flow indicator is disclosed by U.S. Pat. No. 4,745,877 to Chang. Such flow indicators are used in breathing-gas delivery systems. For instance, U.S. Pat. No. 6,386,196 ("Culton" herein) issued to Steven Culton discloses a rotary sight flow indicator incorporated into the flow meter hardware of breathing-gas source.

4. Problems and Limitations of the Prior Art Overcome by the Present Invention

In situations where breathing-gas delivery systems are employed to deliver breathing-gases to patients who are dependent on the breathing-gases, a failure of the system can cause catastrophic results; consequently, the prior art discloses a wide variety of flow-meters and flow indicators. These prior art devices, however, are invariably positioned at or near the source of the breathing-gas; i.e., distal to the gas delivery cannula. The Culton flow-indicator is a good example of a flow-indicator being positioned at the distal end of the system, upstream from the gas delivery cannula. Culton is actually incorporated into the gas source apparatus. Such prior art flow-indicators present a number of problems, some of which are potentially life-threatening, that are overcome by the present invention.

One such problem is that the distally placed flow indicator device can be hidden from the patient because the device is often mounted on a wall, usually behind the patient and often occluded by hanging drapes or other obstructions. Even when those who are caring for the patient can see the flow indicator, the patient himself often cannot. Similarly, flow indicator devices are often connected to portable gas tanks or pumps. Such tanks and pumps are often kept out of the way by placing them on the floor, under the bed, or behind furniture or other obstructions; consequently, it is often hard or impossible to see such flow indicators.

This problem of the patient not being able to see the flow indicator is exacerbated by the fact that many such patients do not have the strength or agility to twist around to see the flow indicators. Because the patient cannot monitor the flow-indicator, should the flow of the breathing-gas flow be interrupted, the patient may not realize it. This is particularly problematic for debilitated patients, who are most in need of a constant flow of breathing-gas.

The present invention solves this problem by providing a breathing-gas flow indicator positioned at or near the proximal end of the gas delivery cannula close to the patient's face, so that the patient and his care-givers can easily see the flow indicator and determine whether breathing-gas is flowing through the gas delivery cannula.

A second potentially dangerous problem of the existing art that is overcome by the present invention is that the distally placed flow indicators are too far "upstream" from the patient to detect flow-failures in most of the system. The amount of information provided by the flow indicator is directly proportional to the distance the flow indicator is from the gas source. In a hospital setting, the length of the gas delivery cannula between the prior art flow indicator and the patient may be several meters. If the gas delivery cannula develops a leak, or a kink, or is severed at some point between the prior art flow indicator located at the gas source and the patient, the prior art flow indicator continues to indicate that the breathing-gas is flowing normally when, in fact, the patient is not receiving any breathing-gas at all. This problem is referred to here as a "false flow signal."

The present invention solves this false flow signal problem by providing a flow indicator placed at or near the proximal end of the gas delivery cannula, near the patient, so that any interruption of flow in the system anywhere between the patient all the way back to and including the gas source is immediately and easily detected.

A third problem with the prior art that is overcome by the present invention is that the prior art flow indicators cannot be easily retrofit into existing systems. The present invention solves this problem by providing a flow indicator that can be easily retrofit into an existing-gas delivery cannula without fittings, clamps, or other hardware. Even if the gas delivery cannula is continuous with the AID, the present invention can be easily frictionally spliced into a convenient point in the gas delivery cannula for easy viewing by the patient.

A fourth problem of the prior art that is overcome by the present invention is that the complexity of the prior art requires excessive manufacturing costs which militate against 1) the device being disposable and 2) wide-spread use and acceptance of the prior art flow indicators. The present invention solves this problem by providing a flow indicator that is sufficiently simple, elegant, and inexpensively produced that it can be widely used to improve the safety of breathing-gas delivery systems. In fact, the present invention can be inexpensively produced in such large quantities as to be used by a single patient for a brief time and then hygienically disposed of. The device can either be manufactured as a separate flow indicator that can be retrofitted into an existing-gas delivery cannula and simply replaced with each new patient, or it can be manufactured as an integral part of the gas delivery cannula, and the entire gas delivery cannula and flow indicator combination replaced when necessary. Thus, the present invention is both personal, in that it is used by only one patient, it is hygienic, and it is disposable.

A fifth problem with the prior art that is overcome by the present invention is that flow indicators incorporated into the breathing-gas source are not portable. This is of concern when a patient is transported from one location to another because during transport the distal end of the gas delivery cannula must be disconnected from the breathing-gas source (and its integrated flow indicator) and re-connected to a portable source of breathing-gas. Consequently, a separate flow indicator is required for the portable breathing-gas source. This problem is solved by the present invention by providing a flow indicator that remains interposed between the AID and the proximal end of the gas delivery cannula when the distal end of the gas delivery cannula is repeatedly connected to and disconnected from different breathing-gas sources. The invention is light enough that it can be worn by an ambulatory patient and still remain fully functional. Even if the patient walks about with a portable tank of gas, the flow indicator remains with the patient to monitor the gas flow.

A sixth problem with the prior art that is overcome by the present invention is that prior art flow indicators cannot be used at night or by the sight impaired. The present invention overcomes this problem in two ways. First, the flow indicator is worn close to the patient's face and can be raised to his eyes and observed in dim light. Second, the flow indicator vibrates gently when gas is flowing through it and the patient can feel these vibrations thereby indicating gas flow even in a completely dark room and even when used by blind patients.

5. Overview of the Invention

Our invention is a flow indicator used in a breathing-gas delivery system, the system comprising a breathing-gas source, an AID, and a gas delivery cannula for conducting breathing-gas from the source to the AID. The gas delivery cannula has a distal end in communication with the source, and a proximal end. The flow indicator has a housing that has at least one transparent housing surface. The housing forms a chamber through which the breathing-gas flows. The housing forms at least one inlet through which the breathing-gas enters the chamber and which is in direct communication with the proximal end of the gas delivery cannula. The housing also forms an outlet through which the breathing-gas exits the chamber, and which is in communication with the AID. The flow indicator has a rotatable member rotatably mounted by mounting means within the chamber and visible from without the chamber through the transparent housing surface.

The rotatable member has at least one rotatable member surface upon which the flowing gas impinges and causes the rotatable member to rotate about its axis of rotation, thereby producing a visible and/or vibrational indication that the breathing-gas is flowing through the gas delivery cannula. Details, variations, and embellishments of the invention are disclosed below.

BRIEF DESCRIPTION OF THE FIGURES

The above and other features and advantages of the invention will become apparent upon considering the following description and the accompanying figures, in which.

DETAILED DESCRIPTION OF THE INVENTION

1. Preferred Embodiments

Figure 1:
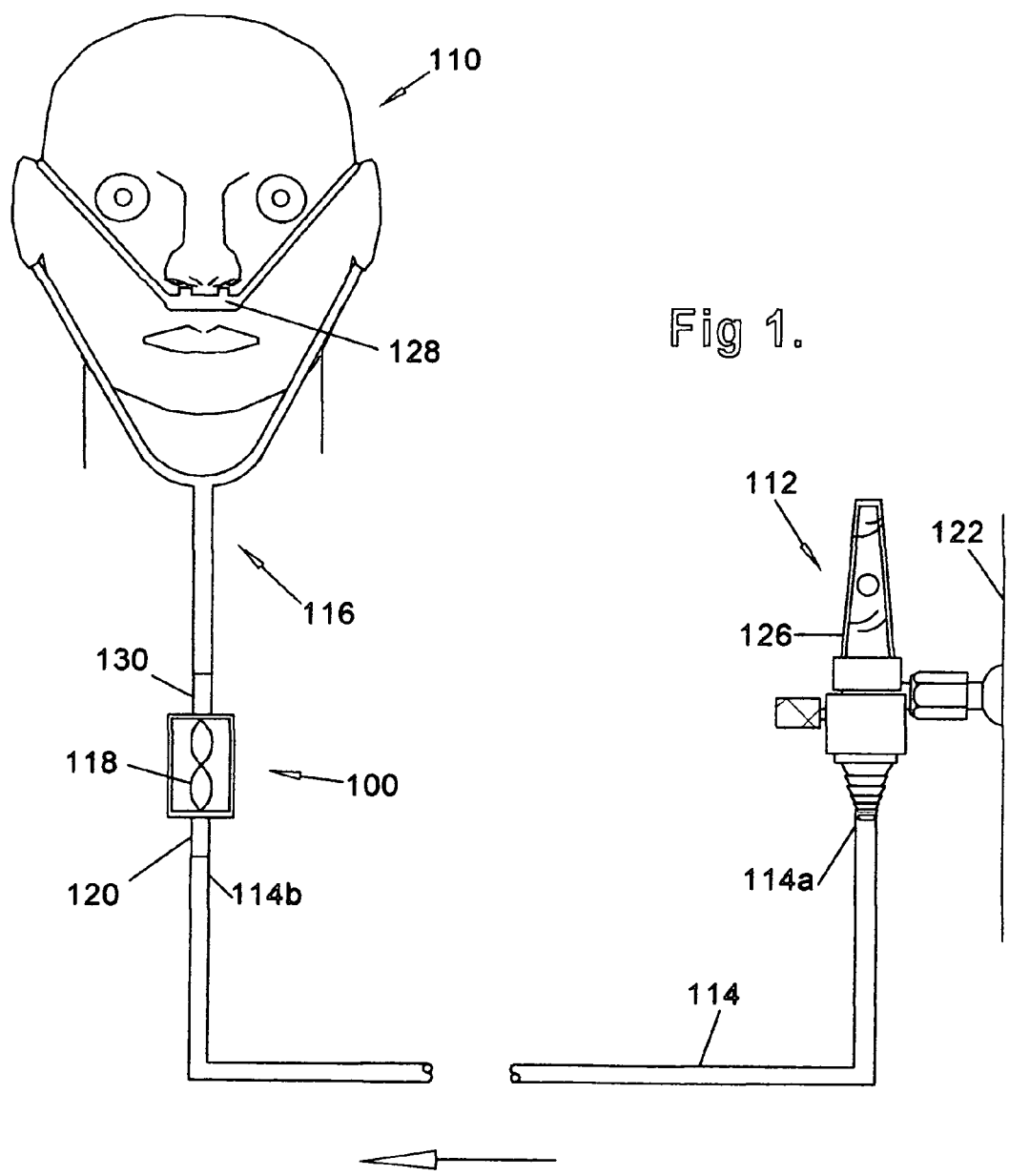
FIG. 1. is a schematic showing a gas delivery system comprising the invention.

FIG. 1. shows a breathing-gas delivery system employing our invention used in conjunction with a prior art gas flow meter 123 even though our invention reduces the need or usefulness of such prior art gas flow meters. Patient 110 receives breathing-gas from breathing-gas source 112, which is a standard gas outlet attached to wall 122. The breathing-gas is conducted from the gas source to our flow indicator 100 through gas delivery cannula 114. Breathing-gas flowing through the gas source flow meter 123 enters gas delivery cannula 114 through the distal end 114a of the gas delivery cannula. The proximal end 114b of the gas delivery cannula is connected to housing inlet 120 of the flow indicator. Thus, the chamber of the flow indicator is in direct communication with the proximal end of the gas delivery cannula so that gas flowing through the gas delivery cannula, as indicated by the arrow, flows into the flow indicator chamber. Breathing-gas flowing through the flow indicator chamber causes rotatable member 118 to rotate about its axis of rotation. The breathing-gas then flows out of the flow indicator chamber through housing outlet 130 and into AID 116, which in FIG. 1. is represented as nasal cannula that transmits the breathing-gas to the outlet ports of nasal clip 128 and into the patients nasal airway.

As shown in FIG. 1, the preferred placement of our invention in the gas delivery system is at the proximal end 114b of the gas delivery cannula 114.

With the flow indicator interposed between the AID and the proximal end of the gas delivery cannula the patient can easily confirm that he is receiving the breathing-gas by visually observing the spinning rotatable member or by feeling the vibrations caused by the spinning rotatable member. It makes no difference whatsoever whether the gas source is behind the patient's head, under the patient's bed, or in another room altogether, with our invention the patient can easily monitor the flow of his breathing-gas through the gas delivery cannula.

Likewise, any persons in the vicinity of the patient can also tell immediately if the breathing-gas is flowing because the flow indicator is positioned within a few inches of the patient's face. It is not necessary to search behind drapes or other obstructions to find a flow-indicator attached to the wall or to try and locate a flow indicator attached to a tank that is hidden beneath a bed or behind a chair.

Figure 2:
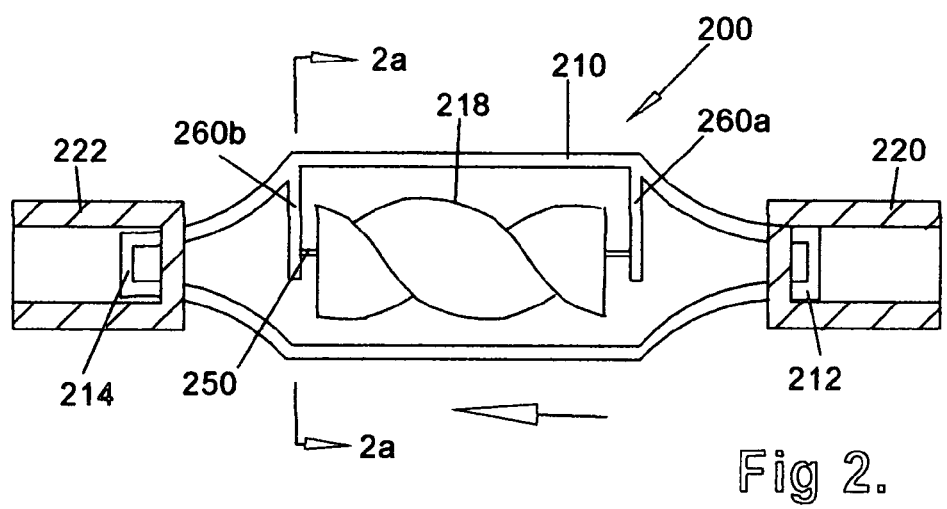
FIG. 2. is a side-elevation of a preferred embodiment of the invention showing a helical rotatable member and a post-type mount.

FIG. 2 shows a side-elevation of first preferred embodiment of the invention comprising a flow indicator in which a helix is employed as a rotatable member.

The flow indicator has a housing 200 that forms a chamber through which the breathing-gas flows. The housing has at least one transparent housing surface 210. In the present embodiment the housing is cylindrical with the entire wall of the cylinder comprising the transparent housing surface, thus providing a 360° view into the chamber.

The flow indicator has a housing inlet 212 and a housing outlet 214, both of which communicate with the chamber. The housing inlet is in direct communication with the proximal end of the gas delivery cannula 220, and the outlet is in direct communication with the distal end 222 of the AID. The flow indicator is thereby interposed between the proximal end of the gas delivery cannula and the distal terminus of the AID. Breathing-gas arrives from the gas source through the gas delivery cannula. The gas flows into housing inlet 212, through the chamber, through housing outlet 214, into the AID, and from there into the patient's airway. The direction of the flow of gas is indicated by the arrow in FIG. 2.

Depending on the type of rotatable member employed and the geometrical shape of the housing, the housing inlet and housing outlet of the chamber may be oriented substantially concentrically relative to one another, or they may be offset in order to effectuate more efficient flow of breathing-gas or to amplify the vibrational signal produced by the spinning rotatable member, as discussed below. The embodiment of FIG. 2 shows a concentric housing inlet and outlet arrangement.

Referring still to FIG. 2, rotatable member 218 is enclosed within the chamber formed by housing 200 and is visible from without the housing through the transparent housing surface 210. The rotatable member has at least one rotatable member surface upon which gas passing through the chamber impinges. In the preferred embodiment of FIG. 2 the rotatable member is in the form of a helix, which comprises a first surface and second surface twisted about an axis of rotation. As can be seen in FIG. 2, the width of the helix at its widest dimension is smaller than the diameter of the housing, thereby allowing free rotation of the helix within the chamber of the housing.

An axle 250 runs through the helix, substantially coincident with the helix's axis of rotation so that the helix rotates freely about the axle. One end of the axle is rotatably attached to a first mount 260a. The other end of the axle is rotatably attached to a second mount 260b.

Figure 2A:
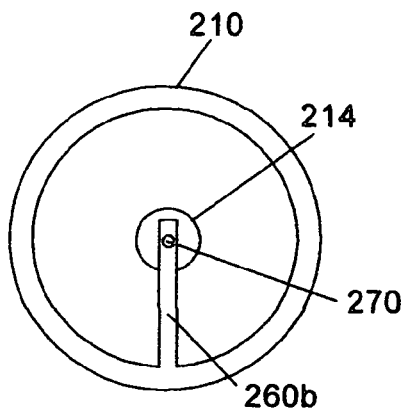
FIG. 2a. is a cross-section of FIG. 2.

FIG. 2a. is a cross-section taken through the invention in order to show the post-style mount 260b adjacent housing outlet 214 and extending into the chamber.

Each end of axle 250 is inserted into an indentation 270 or hole provided in the axle mount for receiving the axle. The diameter of the indentations or holes are sufficiently larger than the diameter of the axle to allow free rotation of the axle within the indentations or holes.

Given the arrangement of the elements of our flow indicator, it can be appreciated that as long as breathing-gas is entering housing inlet 212 and exiting housing outlet 214, the helix 118 will rotate freely about its axis of rotation because the moving breathing-gas impinges upon the surfaces of the helix and causes the helix to rotate on its axle 250. Conversely, when the breathing-gas stops flowing through the flow indicator, there is insufficient force to induce rotation of the helix, and the helix stops rotating. The rotating helix thus becomes a signal indicating that gas is flowing through the gas delivery cannula, with the rate of rotation being proportional to the flow rate of the breathing-gas.

2. Details, Embellishments, and Variations a. Interposing the Flow Indicator Between the AID and Gas Delivery Cannula

It is common in breathing-gas delivery systems for the AID and the gas delivery cannula to be manufactured separately and then reversibly connected at the time of use, the proximal end of the gas delivery cannula being reversibly connected to the distal end of the AID. Our flow indicator can assume three alternative embodiments for interposing the flow indicator between the reversibly connectable gas delivery cannulas and AIDs.

First, the AID can be manufactured with the flow indicator housing outlet 130 irreversibly communicating with AID 116, and housing inlet 120 reversibly connected to the proximal end 114b of the gas delivery cannula 114.

Second, the gas delivery cannula can be manufactured with flow indicator housing inlet irreversibly communicating with the proximal end of the gas delivery cannula, and a housing outlet that can be reversibly connected to the AID.

And third, the flow indicator can be manufactured independently from both the gas delivery cannula and the AID, with the housing inlet and housing outlet being designed to reversibly connect to the proximal end of the gas delivery cannula and the AID, respectively. This embodiment allows the flow indicator to be easily and reversibly frictionally swapped in and out of the breathing-gas delivery system.

In devices in which the gas delivery cannula and AID are manufactured as one continuous piece, an embodiment of the invention is provided in which both the housing inlet and housing outlet accommodate frictional faying to the cut ends of the gas delivery cannula when the gas delivery cannula is cut to receive the flow indicator. The flow indicator is retrofit at any desirable point along the gas delivery cannula simply by cutting the gas delivery cannula and frictionally faying the cut gas delivery cannula ends to the housing inlet and housing outlet.

For the reasons set forth above, the preferred placement of the invention is within easy viewing distance of the patient. However, the invention may be effectively placed at any arbitrary point along the gas delivery cannula, or even spliced into the AID. Of course, the further upstream the flow indicator is placed, the less information it provides about the integrity of the system and the harder it is for the patient to see it.

b. Orientation of the Axis of Rotation.

When employing a helix 218 as a rotatable member as shown in FIG. 2, the preferred orientation of the axis of rotation and, hence, axle 250, is parallel to the flow of breathing-gas. However, other orientations are possible. For example, the helix can be oriented with its axle substantially normal to the flow of breathing-gas through the housing. To accommodate flow-normal orientation, the housing can be spherical with the axle ends mounted in indentations made directly in the housing, thereby dispensing with the need for mounts.

c. Mounting Pins and Mounts

As an alternative to an axle, the rotating means may comprise mounting pins that emanate from each end of the rotating member, substantially coincident with the axis of rotation so that the rotating member can rotate about the mounting pins. The mounting pins are received by the mount indentations 270 or holes.

Figure 2B:
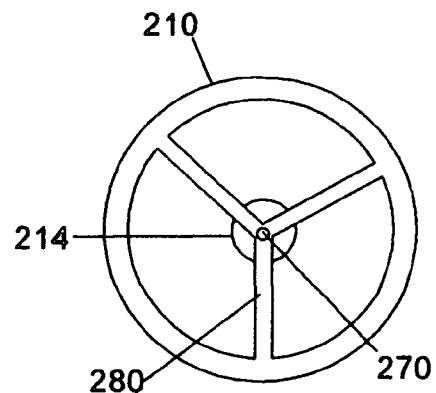
FIG. 2b. is a cross-section of a preferred embodiment of the invention employing a Y type mount.

While mount 270 shown in FIG. 2 and FIG. 2a is a post that extends into the lumen of the chamber, other types of mounts are within the scope of the present disclosure and claims. For instance, FIG. 2b is a cross-section of a flow indicator similar to that shown in FIG. 2, except that the mount is provided by a "Y" piece 280 attached to housing 210. A straight bar extending across the housing is another alternative mount. A variety of approaches will be obvious from this disclosure, and preferences for one type of rotating member and mount over another will be determined largely by manufacturing capabilities, chamber geometry, and costs.

d. Paddle-Wheel Rotatable Member

We anticipate that the rotatable member may assume any shape or form that can be caused to rotate in the presence of flowing-gas. Likewise, while the form of the housing disclosed above is that of an elongate cylinder, we anticipate other forms of housings that will accommodate various types of rotatable members.

Figure 3:
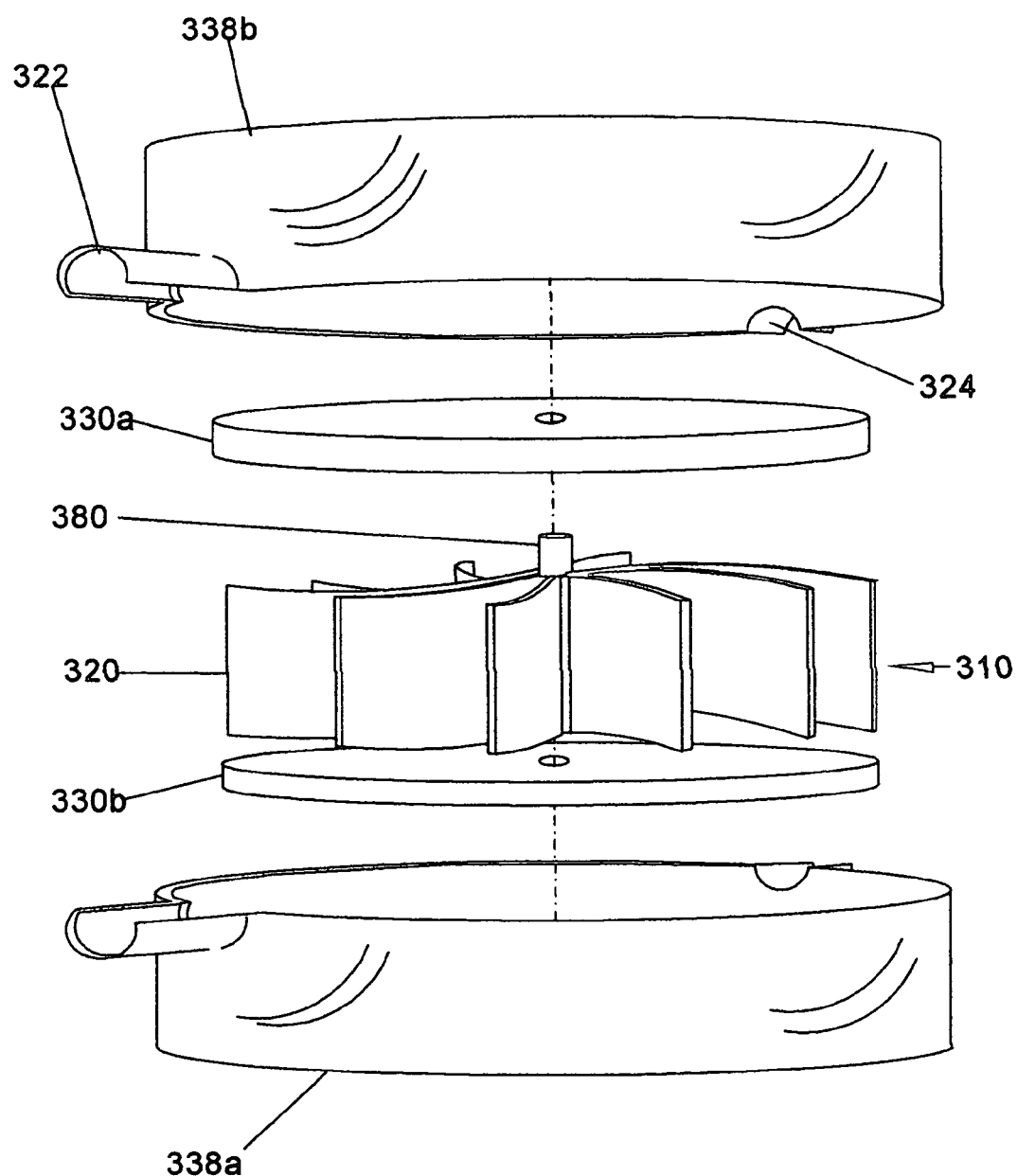
FIG. 3. is an exploded view of a paddle-wheel embodiment of the invention.

For example, FIG. 3 shows an alternative embodiment in which the rotatable member is a paddle-wheel 310 having a plurality of impellers 320 radiating from an axle 380, which axle is oriented normal to the flow of breathing-gas through the housing.

The impellers provide a surface upon which the breathing-gas impinges. Optionally, the impellers are sandwiched between a first disc 330a and a second disc 330b, the discs being oriented parallel to one another. The discs and impellers thus form a paddle-wheel which rotates when breathing-gas impinges upon the impellers. The discs are colored with alternating colors or stripes to facilitate observation of the rotating motion of the rotatable member.

The paddle-wheel is housed in a chamber produced by a lower transparent housing 338a and an upper transparent housing 338b, which form a compressed cylinder with an internal diameter sufficiently larger than the diameter of the paddle-wheel to allow for the free rotation of the paddle-wheel within the chamber. Because the housing is transparent, the impellers, or optionally the discs, are visible from without the housing. Breathing-gas flows into the chamber through housing inlet 324 and flows out through housing outlet 322. Consequently, breathing-gas passing through the chamber impinges upon the impellers of the paddle-wheel, causing it to rotate. The discs can be seen rotating through the transparent housing, thus providing a visual signal that breathing-gas is flowing through the system. Alternatively, the discs can be dispensed with altogether.

e. Amplification of the Visual Signal.

It is desirable to amplify or enhance the visual signal produced by the rotatable member so that the flow indicator may be useful to the sight-impaired and in low light conditions. We anticipate many means of achieving such amplification, such as coloring the rotatable member with an attention-attracting color-scheme. For example, one surface of the helix 118 in FIG. 1. can be colored blue and the other surface colored yellow, such that when the helix rotates at a rotational speed higher than the flicker-rate of the human visual system, the helix appears as green. In addition, at least one surface of the helix is coated with discontinuous bands of luminescent material, or at least one edge is coated with luminescent material, so that rotation of the helix in the dark will be evident due to the illusion of a solid surface of luminescence during rotation, whereas the stationary helix will appear in the dark as discontinuous bands or a single line of luminescence, respectively.

f. Amplification of the Vibrational Signal

Due to practical limitations in the tolerances of the moving parts, the flow indicator vibrates slightly as gas passes through the chamber. For example, a slight deviation from true balance of the rotatable member or a slight angular displacement, or skewing, of the axis of rotation from a line parallel to the flow of the gas through the chamber exacerbates vibration. A small amount of vibration is desirable because it can be felt by the patient when the gas is flowing and, hence, presents a non-visual signal that the patient can use to verify that the gas is flowing, even in the dark or if the patient is sight-impaired or has his eyes closed. Consequently, it is desirable to amplify the vibration caused by the rotating member. This can be done by manufacturing the rotatable member with a slight off-set weighting and/or mounting the rotatable member with its axis of rotation skewed with respect to a line parallel to the flow of the gas through the chamber and/or by providing the mounting indentation 270 or hole with a diameter sufficiently larger than the diameter of the rotatable member axle or mounting pins.

g. Materials

The choice of materials is constrained by functional requirements and design goals of the device. One such functional requirement is that the housing be at least partially transparent. A second functional requirement is that the device be sufficiently lightweight that it can be worn by hanging from a nasal cannula or other AID without pulling the nasal outlets away from the patient's nose. Hence lightweight, transparent materials such as plastic, polycarbonate, or polypropylene are preferred. From the present disclosure, appropriate and suitable materials of construction will be obvious to those skilled in the art.

SUMMARY OF THE INVENTION

The foregoing discloses a novel and useful personal, disposable and wearable flow indicator for monitoring the flow of a breathing-gas through a gas delivery cannula. Upon consideration of these disclosures and claims, many equivalent means of making and practicing the invention will become evident to those skilled in the art. It is understood that the present invention is not limited to the embodiments disclosed above but encompasses any and all embodiments within the scope of the following claims.

We claim:

1. A flow indicator for indicating the flow of breathing-gas through a gas delivery cannula, said flow indicator comprising:
   a. a housing that forms a chamber, said housing comprising a transparent housing surface; and,
   b. at least one rotatable member rotatably mounted within said chamber and visible from without said chamber through said transparent housing surface,
   wherein said flow indicator is interposed between the distal end of an airway interface device (AID) and a proximal end of the gas delivery cannula, and wherein a distal end of the gas delivery cannula is connected to a gas source, and wherein the flow of gas through the gas delivery cannula is indicated by rotation of said rotatable member.

2. The flow indicator of claim 1 wherein said flow indicator is a personal flow indicator.

3. The flow indicator of claim 1 wherein said flow indicator is wearable.

4. The flow indicator of claim 1 wherein an axis of rotation of said rotatable member is skewed with respect to a line parallel to the flow of the breathing-gas through the chamber.

5. The flow indicator of claim 1 wherein said rotatable member comprises off-set weighting.

6. The flow indicator of claim 1 wherein said housing further comprises:
   a. at least one housing inlet, wherein the proximal end of the gas delivery cannula is connected directly to said housing inlet, whereby gas enters said chamber by flowing from the gas source, through the gas delivery cannula into said housing inlet and into said chamber, and,
   b. at least one housing outlet, said housing outlet being in communication with the AID, whereby the gas flows from the chamber, through the housing outlet and into the AID.

7. The flow indicator of claim 6, wherein said housing inlet accommodates frictional faying with the gas delivery cannula proximal end.

8. The flow indicator of claim 6 wherein said housing outlet accommodates frictional faying with the AID.

9. The flow indicator of claim 6, wherein said housing inlet and said housing outlet accommodate frictional faying with cut ends of the gas delivery cannula when the gas delivery cannula is cut to receive the flow indicator.

10. The flow indicator of claim 1 wherein said rotatable member comprises mounting pins.

11. The flow indicator of claim 1 further comprising at least one mount extending into said chamber.

12. The flow indicator of claim 1 further comprising vibrational amplification means for amplifying vibrations caused by the rotation of said rotatable member.

13. The flow indicator of claim 1 wherein said housing inlet is irreversibly connected to the proximal end of the gas delivery cannula, and wherein said housing outlet is reversibly connected to the AID.

14. The flow indicator of claim 1 wherein said housing outlet is irreversibly connected to the AID, and wherein said housing inlet is reversibly connected to the proximal end of the gas delivery cannula.

15. The flow indicator of claim 1 wherein said housing outlet is reversibly connected to the AID, and wherein said housing inlet is reversibly connected to the proximal end of the gas delivery cannula.

16. The flow indicator of claim 1 wherein said rotatable member comprises a paddle-wheel.

17. A method of monitoring the delivery of a gas to a person's airway with the flow indicator of claim 1, said method comprising the steps of:
   (a) interposing the flow indicator between i) the proximal end of the gas delivery cannula, wherein the distal end of the gas delivery cannula is connected to the gas source, and ii) the inlet of an airway interface device (AID); and,
   (b) observing the flow indicator,
   wherein movement of the flow indicator indicates flow of gas through the gas delivery cannula.

18. The method of claim 17 wherein Step (a) comprises the step of frictionally faying an inlet of the flow indicator to the proximal end of the gas-delivery cannula.

19. The method of claim 17 wherein Step (a) comprises the step of frictionally faying an outlet of the flow indicator to the AID.

* * * * *